US00PP18933P2

(12) United States Plant Patent
Korlipara

(10) Patent No.: US PP18,933 P2
(45) Date of Patent: Jun. 17, 2008

(54) ***ECHINACEA PURPUREA* PLANT NAMED 'RASPBERRY TART'**

(50) Latin Name: *Echinacea (purpurea×paradoxa)*
Varietal Denomination: Raspberry Tart

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 41 days.

(21) Appl. No.: 11/705,665

(22) Filed: Feb. 12, 2007

(51) Int. Cl.
*A01H 5/00* (2006.01)

(52) U.S. Cl. ..... Plt./263
(58) Field of Classification Search ..... Plt./263
See application file for complete search history.

*Primary Examiner*—Annette H Para
(74) *Attorney, Agent, or Firm*—Klarquist Sparkman, LLP

(57) ABSTRACT

A new and distinct cultivar of *Echinacea purpurea* plant named 'Raspberry Tart' characterized by smallish inflorescences of intense red purple with a double row of reflexed rays florets, being very floriferous, with a dwarf compact habit, strong upright stems, and good vigor.

1 Drawing Sheet

Botanical denomination: *Echinacea* (*purpurea×paradoxa*).

Variety designation: 'Raspberry Tart'.

The present invention relates to a new and distinct cultivar of *Echinacea* and given the cultivar name 'Raspberry Tart'. *Echinacea* is in the family *Asteraceae.* This new cultivar originated as an F2 selection of a planned cross between *Echinacea purpurea* 'Ruby Giant' (an unpatented plant), as the seed parent, and *Echinacea paradoxa,* as the pollen parent. The F1 seedlings were allowed to open pollinate and the new seedlings were evaluated the next spring. The new cultivar stood out among all the F2 seedings with its intense red purple ray florets.

This new *Echinacea* cultivar is distinguished by:

1. Smallish inflorescences of intense red purple with a double row of reflexed rays florets.
2. Very floriferous.
3. Dwarf compact habit.
4. Strong upright stems.
5. Good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg. shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a one year old *Echinacea purpurea* 'Raspberry Tart' growing in the ground in the show garden in July in Canby, Oreg.

DETAILED PLANT DESCRIPTION

The following is a detailed description of the new *Echinacea purpurea* cultivar based on observations of a one-year-old specimen growing in the ground in full sun under typical outdoor conditions Canby is Zone 8 on the USDA Hardiness map. Temperatures range from a high of 95 degrees F. in August to 32 degrees F. in January. Normal rainfall in Canby is 42.8 inches per year in the trail fields in Canby, Oreg. The color descriptions are all based on The Royal Horticultural Society Colour Chart.

Plant:

*Type.*—Herbaceous perennial.
*Hardiness.*—USDA Zones 4 to 9.
*Size.*—30 cm wide and 48 cm tall to top of inflorescence.
*Form.*—Basal clump.
*Vigor.*—Excellent.
*Roots.*—Fibrous, with many downward growing and few laterals, ivory in color, Yellow White 158D; roots develop easily from cuttings from the crown.

Leaf:

*Type.*—Simple.
*Shape.*—Lanceolate.
*Arrangement.*—Alternate.
*Blade size.*—8 to 12 cm long and 4 cm wide at the widest part.
*Margins.*—Entire, undulate.
*Apex.*—Acuminate.
*Base.*—Attenuate, continuing down petiole.
*Texture.*—Like sandpaper.
*Surface texture.*—Strigose on both sides.
*Venation.*—Pinnate, with three main veins from near the base.
*Color.*—Topside — Deep Green, Yellow Green 147A. Bottom — Yellow Green 147B.
*Petiole description.*—10 cm if basal leaf, 1 to 3.5 cm if cauline leaf and 3.5 mm wide on both, strigose, Yellow Green 147B.

Peduncle description: 46 cm tall and 6 mm wide near flower head, strigose, Yellow Green 144D speckled with dashes of Greyed Purple 187A.

Inflorescence:

*Type.*—Long stalked terminal heads.
*Count of first flush.*—24.

*Size.*—Grows to 6.5 cm wide and 5 cm deep as disc enlarges.

*Ray florets.*—In 2 series, sterile, about 26 ray florets, reflexed, with entire margins, narrowly elliptic, grows to 2.9 cm long, 1 cm wide, glabrous on both sides, the tip two to three toothed, each acuminate. Ray floret, topside — closest to Red Purple 71B but darker and more intense. Ray floret, bottom side — Red Purple 71A.

*Disc.*—Immature disc is flat and Yellow Green 144A with a darker tinge, 16 mm wide, mature disc is conic, 4 cm wide and 2.5 cm deep and Greyed Purple 187A.

*Disc florets.*—11 mm long, Yellow Green 145B, 5 lobed, ovary 3 mm long and White 155A, corolla 6 mm long and 1 mm wide, Yellow Green 144D with lobes Brown 200B; each floret with one persistent, very stiff bract, 12 mm long, Yellow Green 144B tipped with Greyed Purple 187A. Pistil — 7 mm long, extruding, 2-branched stigma, Greyed Purple 187A, style White 155A. Stamen — 5, filaments 5 mm long, Yellow Green 144D, anthers 1 mm long Greyed Purple 187A, pollen Yellow Orange 17A.

*Phyllaries.*—Phyllaries in four leafy series, lobes lanceolate in shape, reflexed, apex acute, margins entire, strigose on back side and glabrous on inside, in an area growing to 3 cm wide, and 1 cm changing with maturity to 5 mm deep, Yellow Green 147B on both sides.

*Bloom period.*—July until frost in Canby, Oreg.

*Fragrance.*—Rose-like.

Seed:

*Fertility.*—Low.

*Number per head.*—1 to 2.

*Size.*—4 mm long and 2 mm wide.

*Color.*—Brown 199D.

Disease and pests: *Echinacea* are susceptible to leaf miners, powdery mildew, bacterial spots, and gray mold. None of these have been observed on plants grown under commercial conditions in Canby, Oreg.

COMPARISONS

Compared to its seed parent, *Echinacea purpurea* 'Ruby Giant', an unpatented plant, the new cultivar has a smaller habit and smaller more intensely colored flowers.

Compared to the pollen parent, *Echinacea paradoxa,* the new cultivar has a smaller habit and intense red purple rather than orange flowers. Both have reflexed ray florets.

Compared to *Echinacea* 'Twilight' (U.S. Plant Pat. No. 17,651), the new cultivar is shorter and more compact.

I claim:

1. A new and distinct cultivar of *Echinacea purpurea* plant as herein illustrated and described.

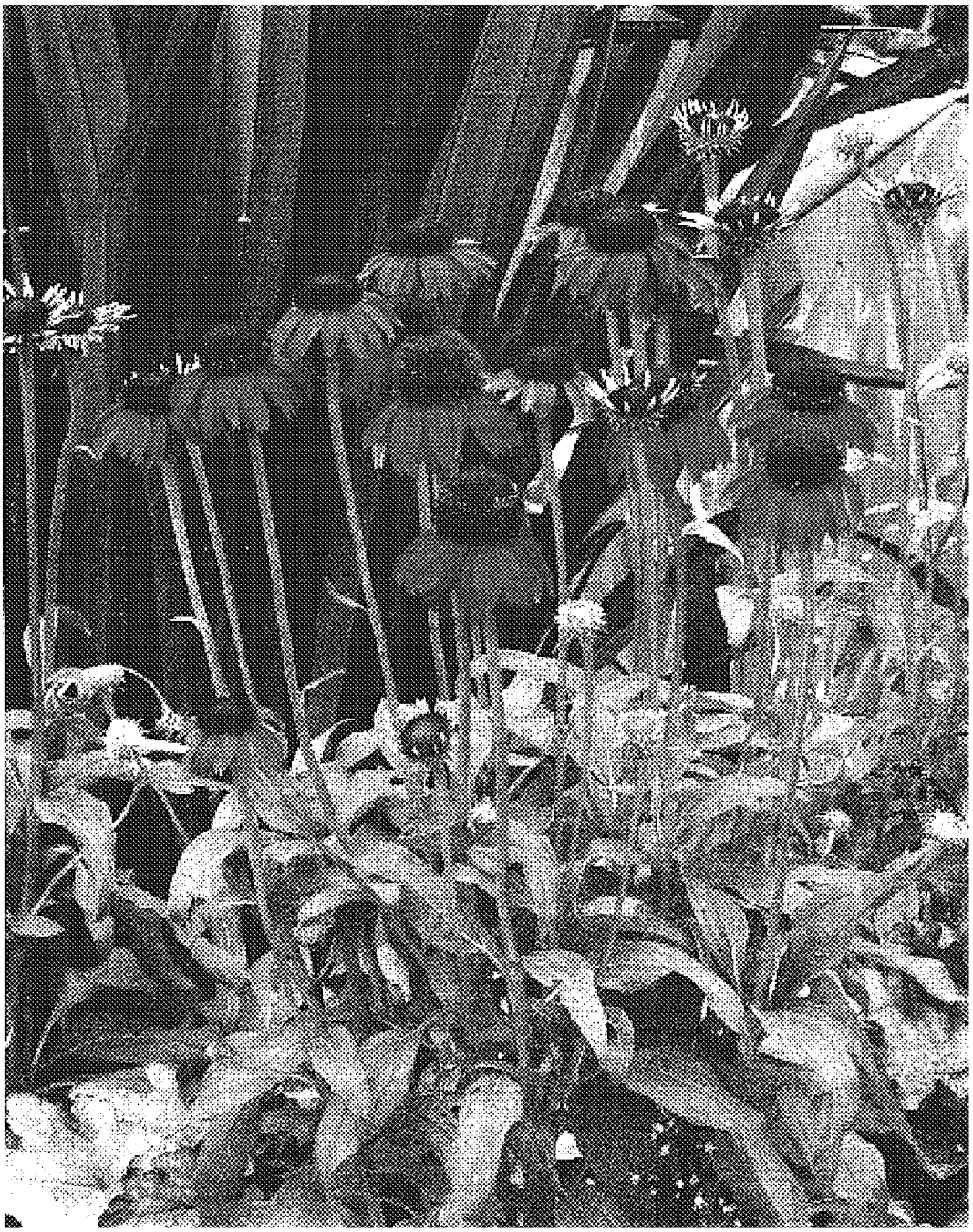

* * * * *